US012755362B2

(12) United States Patent
Lee et al.

(10) Patent No.: US 12,755,362 B2
(45) Date of Patent: Oct. 6, 2026

(54) APPARATUS FOR ANALYZING CROP GROWTH INFORMATION THROUGH MULTIPLE COMPOSITE IMAGES AND METHOD FOR EXPLORING PLANT PHENOTYPES USING THE SAME

(71) Applicant: INDUSTRY-ACADEMIC COOPERATION FOUNDATION OF SUNCHON NATIONAL UNIVERSITY, Seoul (KR)

(72) Inventors: Meong Hun Lee, Seoul (KR); Hyun Yoe, Seoul (KR); Seung Jae Kim, Seoul (KR); Hwa Yeong Shin, Seoul (KR); Dae Han Park, Seoul (KR); Hyeon O Choe, Seoul (KR); Sang Min Lim, Seoul (KR); Gwang Hoon Jung, Seoul (KR); Jae Heon Kim, Seoul (KR); Kyeong Il Ko, Seoul (KR); Kwang Ho Yang, Seoul (KR); Hyun Jun Kim, Seoul (KR)

(73) Assignee: INDUSTRY-ACADEMIC COOPERATION FOUNDATION OF SUNCHON NATIONAL UNIVERSITY, Seoul (KR)

( * ) Notice: Subject to any disclaimer, the term of this patent is extended or adjusted under 35 U.S.C. 154(b) by 160 days.

(21) Appl. No.: 18/956,197

(22) Filed: Nov. 22, 2024

(65) Prior Publication Data

US 2026/0120261 A1 Apr. 30, 2026

(30) Foreign Application Priority Data

Oct. 24, 2024 (KR) ........................ 10-2024-0146569

(51) Int. Cl.
*G06T 7/00* (2017.01)
*G01N 33/00* (2006.01)

(52) U.S. Cl.
CPC ....... *G06T 7/0002* (2013.01); *G01N 33/0098* (2013.01); *G06T 2207/10024* (2013.01);
(Continued)

(58) Field of Classification Search
None
See application file for complete search history.

(56) References Cited

U.S. PATENT DOCUMENTS 12,062,236 B2 * 8/2024 Migdal ................. G06F 16/739
2014/0055573 A1 * 2/2014 Lee ........................... G06T 7/70
348/47

(Continued)

FOREIGN PATENT DOCUMENTS

KR 102032499 B1 10/2019
KR 1020230102860 A 7/2023

(Continued)

*Primary Examiner* — Talha M Nawaz
(74) *Attorney, Agent, or Firm* — Dinsmore & Shohl LLP; Yongsok Choi, Esq.

(57) ABSTRACT

The present disclosure provides a technique that has the effect of increasing the profitability of a smart farm by providing a means of capturing video images of crops using an RGB camera, a thermal imaging camera, and a hyper-spectral camera; distinguishing the phenotype of crops using the captured RGB images; enabling growers to select and cultivate the genetic characteristics of crops according to the phenotype of crops even for the same crop by region, climate, and terrain of the smart farm by analyzing the thermal and hyperspectral images and the composite images thereof to distinguish environmental resistance such as veg-etation index and water stress by the phenotype of crops.

6 Claims, 11 Drawing Sheets

(52) U.S. Cl.
CPC ............... *G06T 2207/10036* (2013.01); *G06T 2207/10048* (2013.01); *G06T 2207/20221* (2013.01); *G06T 2207/30188* (2013.01)

(56) References Cited

U.S. PATENT DOCUMENTS

| | | | | |
|---|---|---|---|---|
| 2018/0268583 | A1* | 9/2018 | Noh | H04N 19/597 |
| 2026/0120261 | A1* | 4/2026 | Lee | G06T 7/0002 |

FOREIGN PATENT DOCUMENTS

| | | | |
|---|---|---|---|
| KR | 102630133 | B1 | 1/2024 |
| KR | 1020240069042 | A | 5/2024 |

* cited by examiner

APPARATUS FOR ANALYZING CROP GROWTH INFORMATION THROUGH MULTIPLE COMPOSITE IMAGES AND METHOD FOR EXPLORING PLANT PHENOTYPES USING THE SAME

CROSS-REFERENCE TO RELATED APPLICATION

This application claims priority to Korean Patent Application No. 10-2024-0146569 filed on Oct. 24, 2024, the entire contents of which are herein incorporated by reference.

TECHNICAL FIELD

The present disclosure relates to an apparatus for analyzing crop growth information through multiple composite images, and more particularly, to a technique for finding a phenotype of a crop by combining image data that is crop growth phenotype data regarding the crop and growth information regarding the crop.

DESCRIPTION OF THE RELATED ART

In the related art before the filing of the present disclosure discloses method for measuring plant phenotypes using images. In this technique, a technique for measuring a plant phenotype for a vegetation index of a crop using image processing technique is disclosed.

Another related art discloses a deep learning-based crop growth diagnostic method and system. The technique comprises acquiring a number of stress phenotype RGB images of the growth state of soybean crops according to nutrient stress, and using them as training data to train a learning model to build an object recognition model to diagnose the growth state of soybean crop.

REFERENCES IN RELATED ART

Registered Korean Patent Publication No. 10-2630133

Korean Patent Application Publication No. 10-2024-0106683

DISCLOSURE OF THE INVENTION

Technical Goals

In order to grow crops successfully in a uniform cultivation system such as a smart farm, it is essential to select and grow crops with the right traits for the location and region. To do this, it is necessary to know the exact genetics of the crop according to its phenotype. This requires monitoring the growth of the crop, and in the process of monitoring the growth of crop, it is necessary to classify and identify the genetic properties of crops according to their phenotypes, and using the matching relationship between the phenotype and genetic properties of these crops, it may be possible to select and grow appropriate crops for smart farms by region, climate, and altitude.

Accurate monitoring of crop growth to achieve the above objectives is essential to determine the physiological and ecological responses of crops to environmental stresses that they may be subjected to in their growing environment, such as drought, global warming, soil salinity, heavy metals, and the like. Biomass, which is considered the most important measure of a crop's growth response, may not be measured non-destructively, so to observe changes in plant growth over time, multiple replicates per treatment were used from the beginning of the experiment, and the relative growth method was used to select traits (such as stem length, internode length, leaf area, and the like) that may be measured without harvesting the plants, and the relationship between the traits and biomass was obtained to estimate the change in biomass.

To this end, based on the information input from Red Green Blue (RGB), thermal and hyperspectral imaging apparatuses of crops, we aim to provide a technique that predicts crop growth and yield based on the images. The multi composite imaging apparatus of the present disclosure composes image information from two or more of thermal, hyperspectral and RGB image acquisition apparatuses, and uses additional information through image composite in addition to analysis through image acquisition in the related art to extract information related to effective crop growth compared to techniques in the related art, and combines it with phenotypes to provide means to select the most suitable crop in the area where the smart farm is located.

The present disclosure aims to provide a technique that may be used to study the physiological and ecological responses of crops to extreme weather and environmental stresses by selecting traits (such as stem length, internode length, leaf area, and the like) that may be measured without harvesting plants using relative growth method (allometry), and predicting growth by finding the relationship between the traits and biomass.

Technical Solutions

The present disclosure provides a means below of solving the above matters.

An apparatus for analyzing crop growth information through multiple composite images and method for exploring plant phenotypes using the same, are provided, characterized in that the apparatus includes:

in order for taking multiple composite images of the crops, a thermal imaging camera and a temperature analysis part for analyzing the temperature from images acquired by the thermal imaging camera; and a hyperspectral camera and a spectrum analysis part for analyzing a range of spectrum from images acquired by the hyperspectral camera; and a RGB camera and a crop recognition part that recognizes crops separately from the background from the images acquired by the RGB camera; and an image merging part for generating a single merged image from an image acquired by the thermal imaging camera, an image acquired by the hyperspectral camera and an image acquired by the RGB camera; and an image compositing part that creates multiple composite images using the images merged from the image merging part; and a data storage part that stores the image composited by the image compositing part and the merged image merged by the image merging part; and an artificial intelligence analysis part that classifies the merged images stored in the data storage part by the phenotype of the crop using the images stored in the data storage part and builds a database (DB).

An apparatus for analyzing crop growth information through multiple composite images and method for exploring plant phenotypes using the same, are provided, characterized in that the image compositing part includes:

a heat stress analysis part that analyses heat stress using the thermal image and the crop data recognized by the crop recognition part; and the RGB analysis part performs RGB analysis using the RGB image.

Also, an apparatus for analyzing crop growth information through multiple composite images and method for exploring plant phenotypes using the same, are provided, characterized in that the RGB analysis part extracts the trait information of the crop to analyze the characteristics of the crop according to the phenotype of the crop.

Also, an apparatus for analyzing crop growth information through multiple composite images and method for exploring plant phenotypes using the same, are provided, characterized in that the trait information of the crops may include stem length, internode length, leaf width and leaf length.

Also, an apparatus for analyzing crop growth information through multiple composite images and method for exploring plant phenotypes using the same, are provided, characterized in that the information combined with the crop trait information may include fruit size, number, heat stress and the vegetation index.

Also, an apparatus for analyzing crop growth information through multiple composite images and method for exploring plant phenotypes using the same, are provided, characterized in that the data storage part may store the merged image, along with a crop type, a water stress index, growth index, a leaf length, a leaf width, a leaf height, a crop surface temperature, a medium temperature, images date, an external temperature and humidity, a smart farm internal temperature and humidity, a crop number, and a crop location.

Effects

The disclosed configuration of the present disclosure has a technique that has the effect of increasing the profitability of smart farms by classifying cultivated crops using trait information such as stem length, internode length, leaf width, leaf length, and the like of the crops cultivated in the smart farm; monitoring the suitability of the cultivation environment such as vegetation information, water stress, and the like by using RGB images, thermal images, and hyperspectral images as they are, or by compositing two or more of these images; acquiring and providing data that combines the phenotype of crops, the profitability of crops, and the adaptability of crops to the growing environment by combining the relevance of yields related to future profits so that growers may be able to select and grow the genetic characteristics of crops according to the phenotype of crops even for the same crop by region, climate, and terrain.

DETAILED DESCRIPTION FOR CARRYING OUT THE INVENTION

The effect of the present disclosure is explained below with reference to drawings.

Accurate monitoring of crop growth is essential for studying the physiological and ecological responses of crops to environmental stresses such as drought, salinity, heavy metals and the like. Biomass, which is considered the most important measure of a crop's growth response, may not be measured non-destructively, so to observe changes in plant growth over time, multiple replicates per treatment were used from the beginning of the experiment, and the relative growth method was used to select traits (such as stem length, internode length, leaf area, and the like) that may be measured without harvesting the plants, and the relationship between the traits and biomass was obtained to estimate the change in biomass.

In crops, leaf area is closely related to aboveground biomass, so changes in biomass may be estimated if leaf area may be accurately measured. The present disclosure seeks to predict crop growth and yield using images captured by RGB, thermal, and hyperspectral imaging apparatuses. To this end, it is aimed to provide a technique to acquire information related to crop growth as accurately as possible by converting images taken by the RGB, thermal, and hyperspectral imaging apparatuses into single or multiple composite images.

Figure 1:
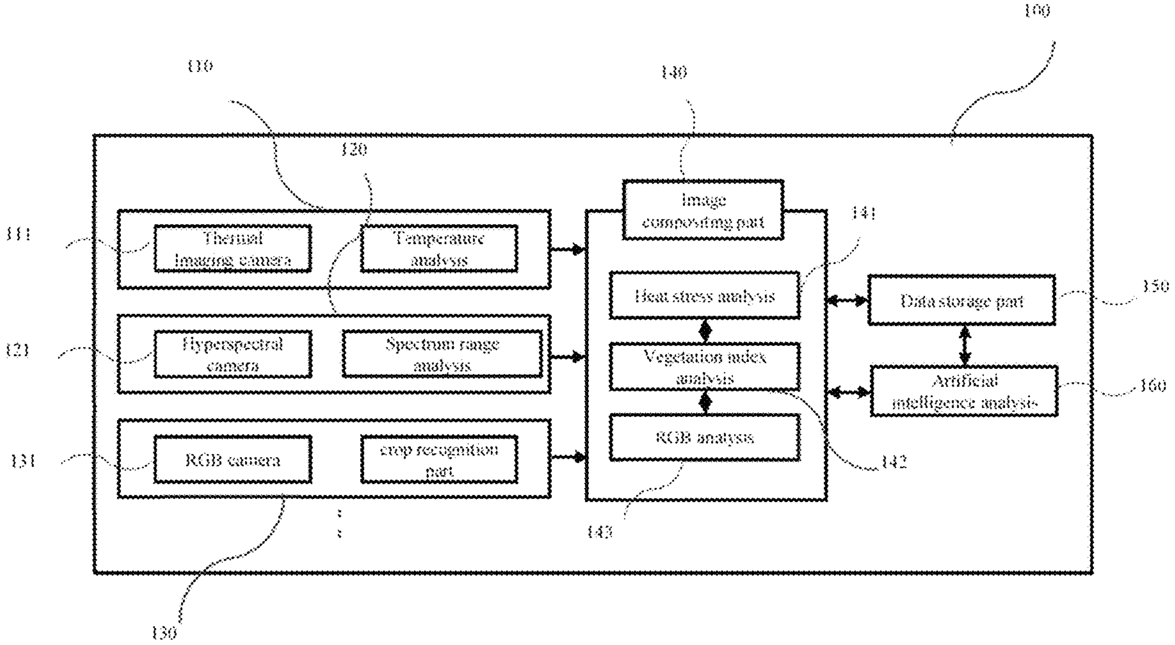
FIG. 1 is a system configuration diagram of the entire system of the crop growth information analysis apparatus using multiple composite images of the present disclosure.

FIG. 1 is a system configuration diagram of the entire system of the crop growth information analysis apparatus using multiple composite images of the present disclosure.

The apparatus 100 includes: in order for taking multiple composite images of the crops, a thermal imaging camera and a temperature analysis part for analyzing the temperature from images acquired by the thermal imaging camera; a hyperspectral camera and a spectrum analysis part for analyzing a range of spectrum from images acquired by the hyperspectral camera; and a RGB camera and a crop recognition part that recognizes crops separately from the background from the images acquired by the RGB camera. The apparatus may include one or more processors for executing program instructions.

The temperature analysis part 110, the spectrum range analysis part 120, the crop recognition part 130, the image composition part 140, the heat stress analysis part 141, the vegetation index analysis part 142, the RGB analysis part 143, and the artificial intelligence analysis part 160 may be program modules to be executed by the one or more processors. The program modules may be included in the apparatus 100 in the form of operating systems, application program modules, and other program modules, while they may be physically stored in a variety of commonly known storage devices. Such program modules may include, but are not limited to, routines, subroutines, programs, objects, components, and data structures for performing specific tasks or executing specific abstract data types according to the invention as will be described below.

The temperature analysis part 110 measures the temperature of the crop surface and the temperature of the medium, and the like through a thermal imaging camera 111. The thermal imaging camera captures environmental changes such as water stress in the crop to provide essential information to assess the condition of the crop. Essential information may include leaf drying and no leaf temperature changes due to pathogen infection.

The thermal imaging camera 111 utilizes infrared technique to detect the temperature distribution of the crop, and may identify physiological changes in the crop due to a lack or excess of water.

The spectral range analysis part 120 may measure the vegetation index (NDVI, and the like) and water stress of the crop through hyperspectral images taken using the hyperspectral camera 121, and may detect pests and pest eggs by varying the image acquisition wavelength. Hyperspectral images may be used to analyze the photosynthetic capacity and growth status of crops. In one example, hyperspectral images of various wavelengths may be acquired, and the chlorophyll content and water status of the crop may be analyzed according to the acquired wavelength bands. These analyses may identify crops that are more resistant to pests and environmental stresses due to the supply of heat and water, and by identifying the phenotype of the crop, genotypes with environmental resistance may be identified based on the phenotype of the crop.

The crop recognition part 130 measures the size and shape of the crop (for example, fruit size, leaf length, leaf width, leaf height, and the like) using the RGB camera 131. Through this, it is possible to determine how well the crop is growing and whether there are any visible pests. RGB images use light in visually detectable areas to determine the appearance of crops, and are used to monitor growth rate and size changes, and the crop recognition methods may use traditional image processing methods and modern artificial intelligence techniques such as YOLO (You Only Look Once V7.0). The present disclosure is configured to measure fruit size, leaf length, leaf width, leaf height, and the like in a single image by using additional training data to the above artificial intelligence recognition method, and to include location information of the crop in the image. In addition, the RGB camera was used to capture the R (red), G (green), and B (blue) images as separate charge-coupled device (CCD) elements and saved as bit map (BMP) images with no image loss for further analysis.

The image compositing part 140 combines the data obtained from the thermal imaging camera 111, the hyperspectral camera 121, and the RGB camera 131 in the image compositing part to generate stereo images. Each image provides different information, which may be composed to provide a more comprehensive analysis of crop status. The stereo image composite combines two or more images from the same location to provide three-dimensional information, which may be used to estimate more precise growth information.

Furthermore, in order to facilitate the management and use of the multi-composite image file of the present disclosure, the RGB, thermal, and hyperspectral images are organized to be distinguished using headers, and are merged into a single file for storage and use. RGB images are acquired using an apparatus in which the CCD element separates R, G, and B and acquires and stores each as a lossless image in BMP format, thermal images are also stored as BMP lossless images, and hyperspectral images are stored as the number of wavelength bands captured by hyperspectral imaging.

The above header is a header that identifies the image as a multi-composite associative image, and it is configured that the file starts with a Multi Coposion Image (MCI), followed by the alphabet "R"+R image start position, alphabet "R"+G image start position, alphabet "R"+B image start position to indicate the RGB image merge location; alphabet "I"+image start position to indicate the infrared merge location; alphabet "U"+number of images, alphabet "U"+1st image, . . . , alphabet "U"+last image position, image data from RGB image, . . . , the last hyperspectral image data, and the image termination tag "END" to indicate the hyperspectral image merge location, so that multiple composite images consisting of three different image acquisition apparatuses are merged into a single file for easy use. After "END" above, additional information may be stored, and each data field may be used by adding any combination of alphabetic and numeric characters, separated by 8 characters. In particular, the phenotype of a crop may be configured to be distinguished by 8 letters of the alphabet after "END" above, and to be added an additional 8 numbers.

It is stored in a data storage part 150 that stores the image composed by the image compositing part and the merged image merged by the image merging part, and is equipped with an artificial intelligence (AI) analysis part 160 that classifies the merged image stored in the data storage part 150 by the phenotype of the crop using the image stored in the data storage part and builds a DB. The data storage part 150 may comprise RAM, ROM, flash memories, hard drives, or any device capable of storing machine-readable and executable instructions such that the machine-readable and executable instructions can be accessed by the one or more processors.

The image compositing part comprises a heat stress analysis part 141 for analyzing heat stress using the thermal image and the crop data recognized by the crop recognition part, a vegetation index analysis part 142 for analyzing the vegetation index using the hyperspectral image and the crop data recognized by the crop recognition part, and an RGB analysis part 143 for performing RGB analysis using the RGB image.

An AI analysis part above 160. The stored data is analyzed by the AI model.

The AI analysis part 160 may classify the RGB images, thermal images, and hyperspectral images stored in the data storage part into phenotypes such as stem length, internode length, leaf width, and leaf length of the crop, re-generate the relevance of the classified phenotypes, classify them from 5 to 20 according to the needs of the user, and combine the fruit size, number of fruits, water stress, and vegetation index as attribute data to provide information for the farmer to select and cultivate the phenotype of the crop in the future.

Further, the artificial intelligence analysis part 160 may comprise a crop growth status determination part, a pest determination part, and a water stress level determination part, and may comprise a model trained using the multiple composite images. To do this, deep learning techniques from the field of artificial intelligence may be also used. In other words, the AI algorithms based on deep learning may analyze multiple composite images and provide users with pest diagnosis, growth trend analysis, and environmental stress response method.

Figure 2:
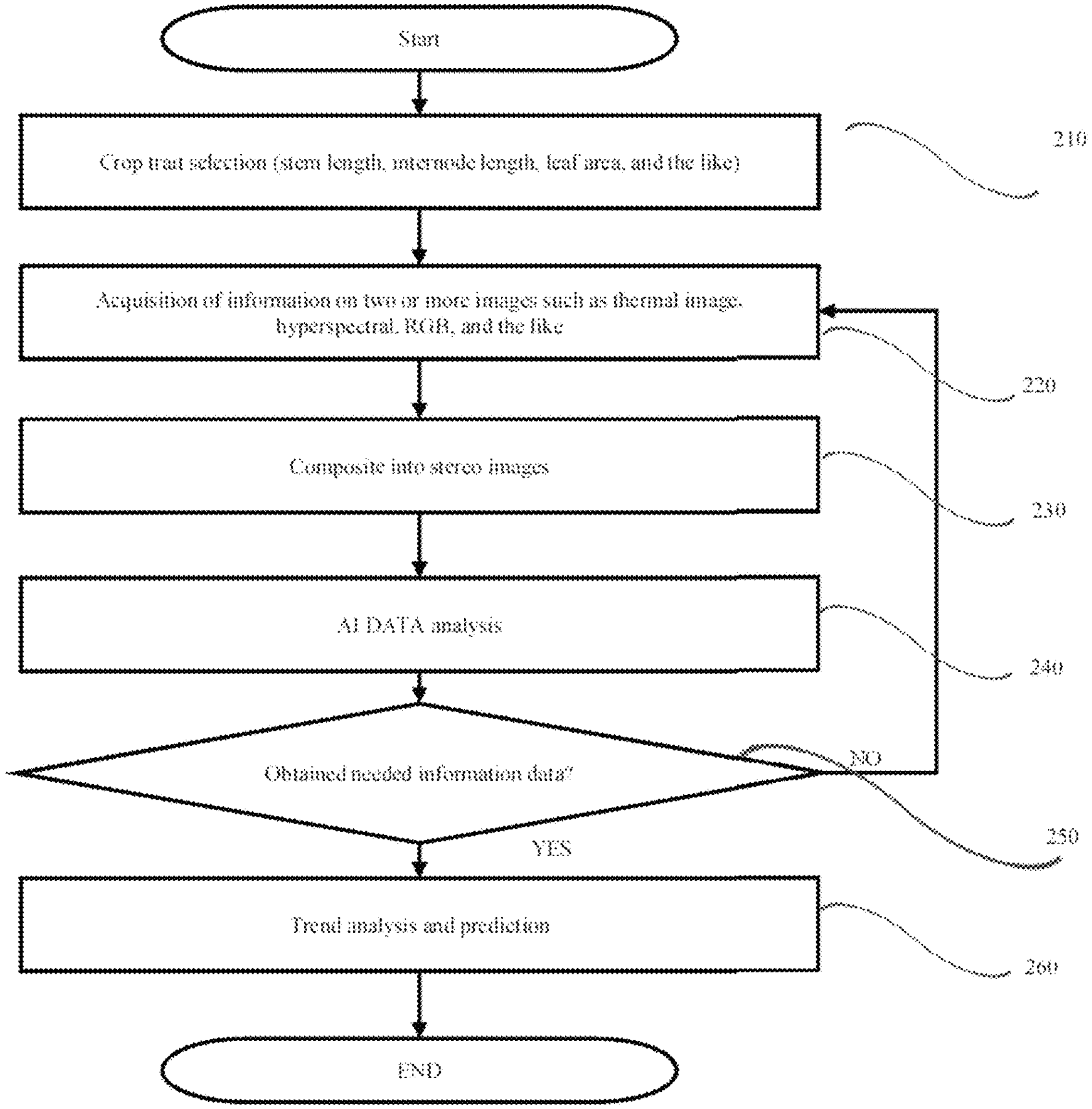
FIG. 2 is a flowchart illustrating a method of collecting multiple composite images using the crop growth information analysis apparatus through multiple composite images for collecting crop trait data of the present disclosure.

FIG. 2 is a flowchart illustrating a method of collecting multiple composite images using the crop growth information analysis apparatus through multiple composite images for collecting crop trait data of the present disclosure. A flowchart of trend analysis and prediction using the artificial intelligence data analysis part of the present disclosure is shown. RGB, thermal and hyperspectral images are acquired and composed into a stereo image. Unlike stereo images in the related art, the stereo image is generated from images taken of a single object using two different image acquisition apparatuses. This allows for the comparison and analysis of images acquired by two different methods. The generated stereo image is analyzed by the AI data analysis part. Basically, the above AI data analysis part includes “crop growth status determination part”, “pest determination part”, and “water stress level determination part”. For this purpose, the growth status of crops is determined by judging the vertical growth from the images measured for each individual crop, pests are determined from the image data of the leaf circumference of the crop, and the level of water stress is mainly determined using thermal images and hyperspectral images. The AI data analysis part may be configured using deep learning technique and image processing technique, and may be implemented by using a library distributed in the form of a package or additional learning in an AI classification program. However, it is a unique crop artificial intelligence analysis technique of the present disclosure to photograph a crop in two or more different ways and make a stereo image of the crop and use it for learning, to identify the growth status of the crop by finding the speed of the crop and the damage of the growth point using the stereo image composed of the RGB image and the thermal image, to measure or predict the pest of the crop using the stereo image composed of the RGB image and the hyperspectral image, and to generate a water stress index using the stereo composite image of the thermal image and the hyperspectral image.

Figure 3:
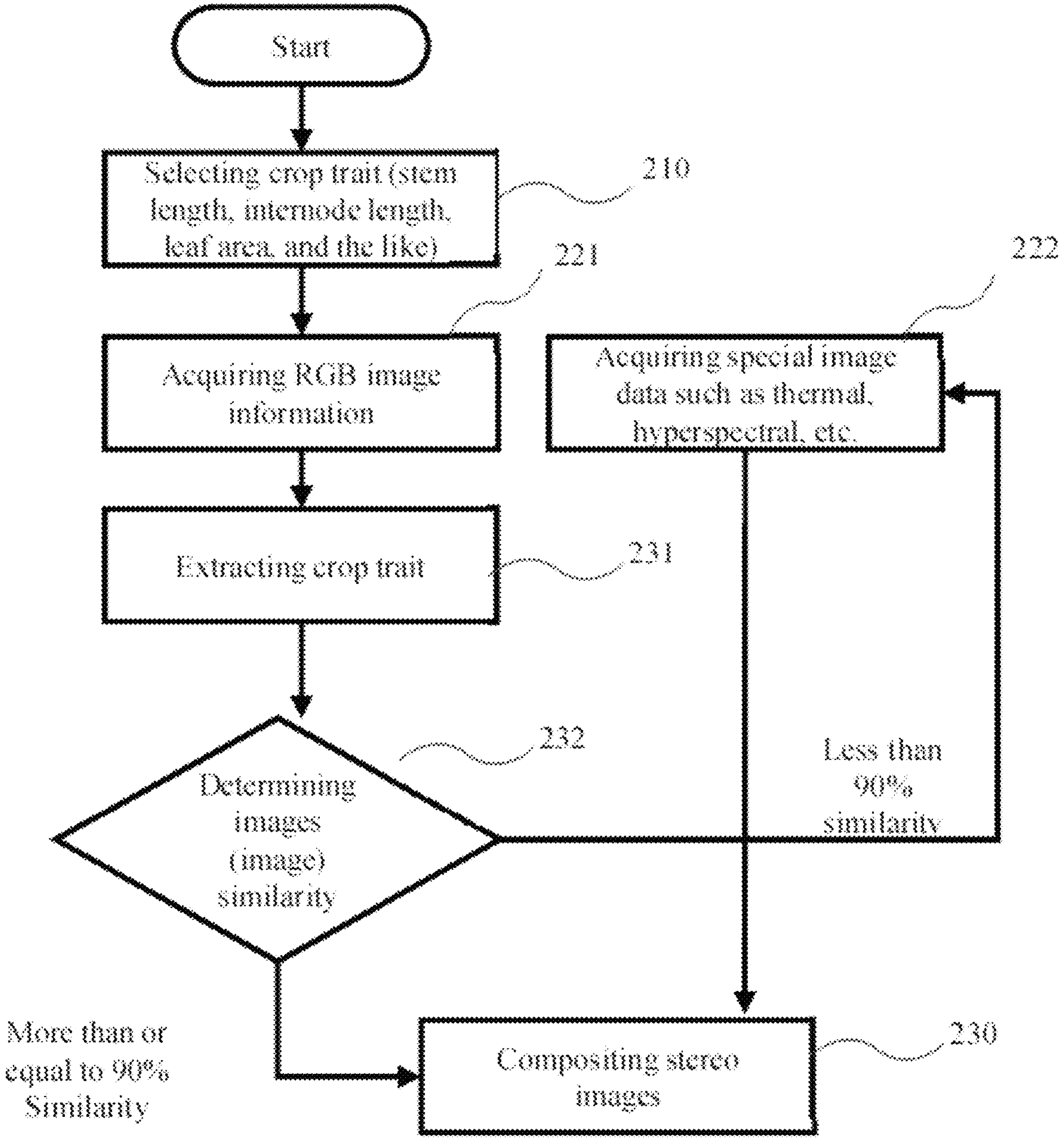
FIG. 3 is a flowchart illustrating a data collection method for collecting data per phenotype of a crop using the crop growth information analysis apparatus through multiple composite images of the present disclosure.

FIG. 3 is a flowchart illustrating a data collection method for collecting data per phenotype of a crop using the crop growth information analysis apparatus through multiple composite images of the present disclosure. The process of acquiring RGB, thermal, and hyperspectral images of crop phenotypes (stem length, internode length, leaf area, and the like) and generating composite images from them is illustrated. If the images acquired by the two different apparatuses are not similar, the thermal and hyperspectral images are re-acquired by adjusting the acquisition conditions, and the images are composed when the image similarity is greater than 90%. The composited image was composited into a stereo image because it is convenient for future use.

Figure 4:
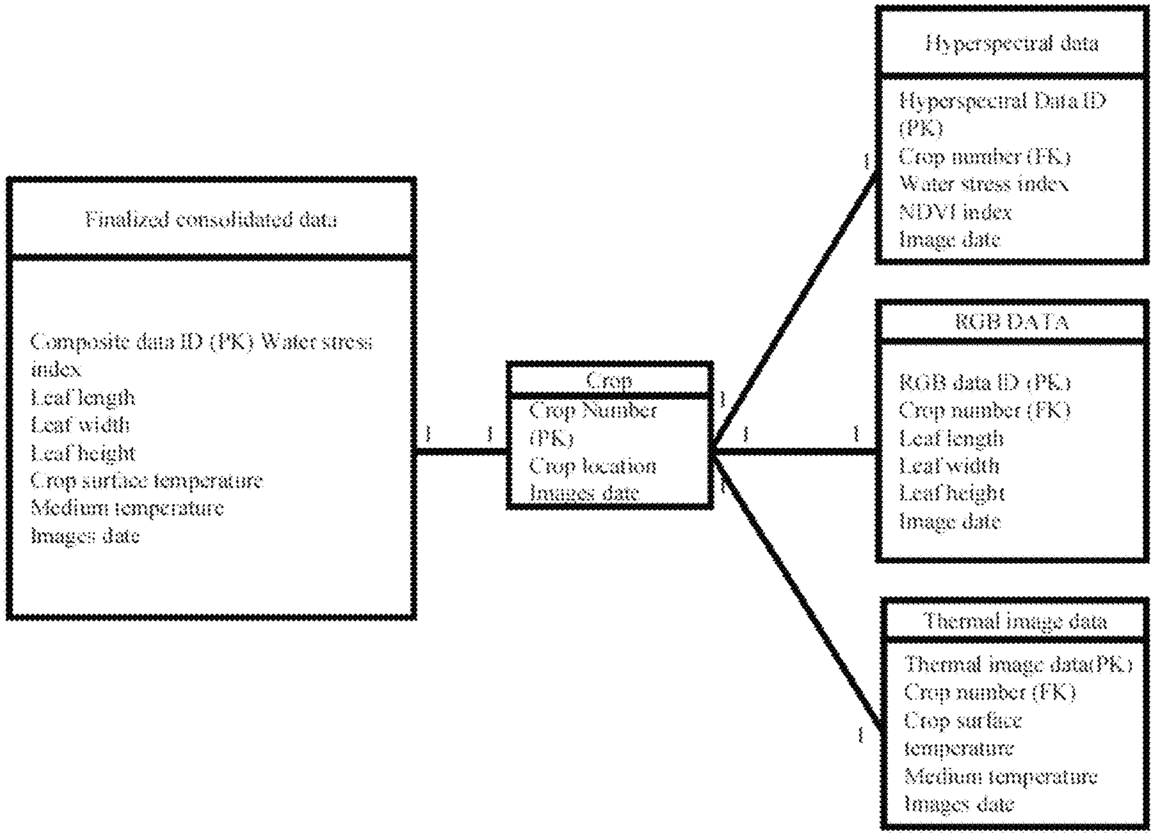
FIG. 4 shows a data structure for collecting and DBing phenotypic data of crops using the crop growth information analysis apparatus through multiple composite images of the present disclosure.

FIG. 4 shows a data structure for collecting and DBing phenotypic data of crops using the crop growth information analysis apparatus through multiple composite images of the present disclosure. The abbreviations PK means primary key, FK means foreign key, and it is used to refer to the PK key of another database, and 1:1 means that there is a 1:1 correspondence between the data in the database.

Figure 5:
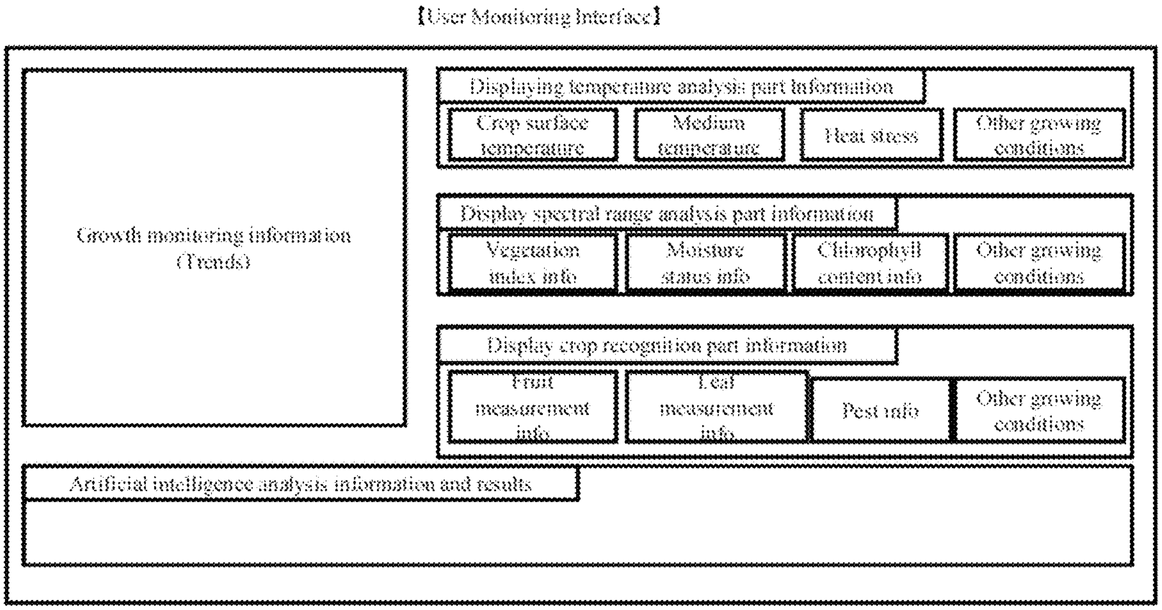
FIG. 5 illustrates a user screen for collecting and DBing phenotypic data of a crop using the crop growth information analysis apparatus through multiple composite images of the present disclosure and displaying it on the user screen.

FIG. 5 illustrates a user screen for collecting and DBing phenotypic data of a crop using the crop growth information analysis apparatus through multiple composite images of the present disclosure and displaying it on the user screen. The user may access the database to select and view the growth trend of each crop or the entire smart farm, and the analysis is displayed through RGB images, thermal images, and hyperspectral images according to the user’s selection. In particular, the AI analysis and results include simple image analysis, as well as analysis using stereo images, which are composites of images taken by two or more methods.

Figure 6:
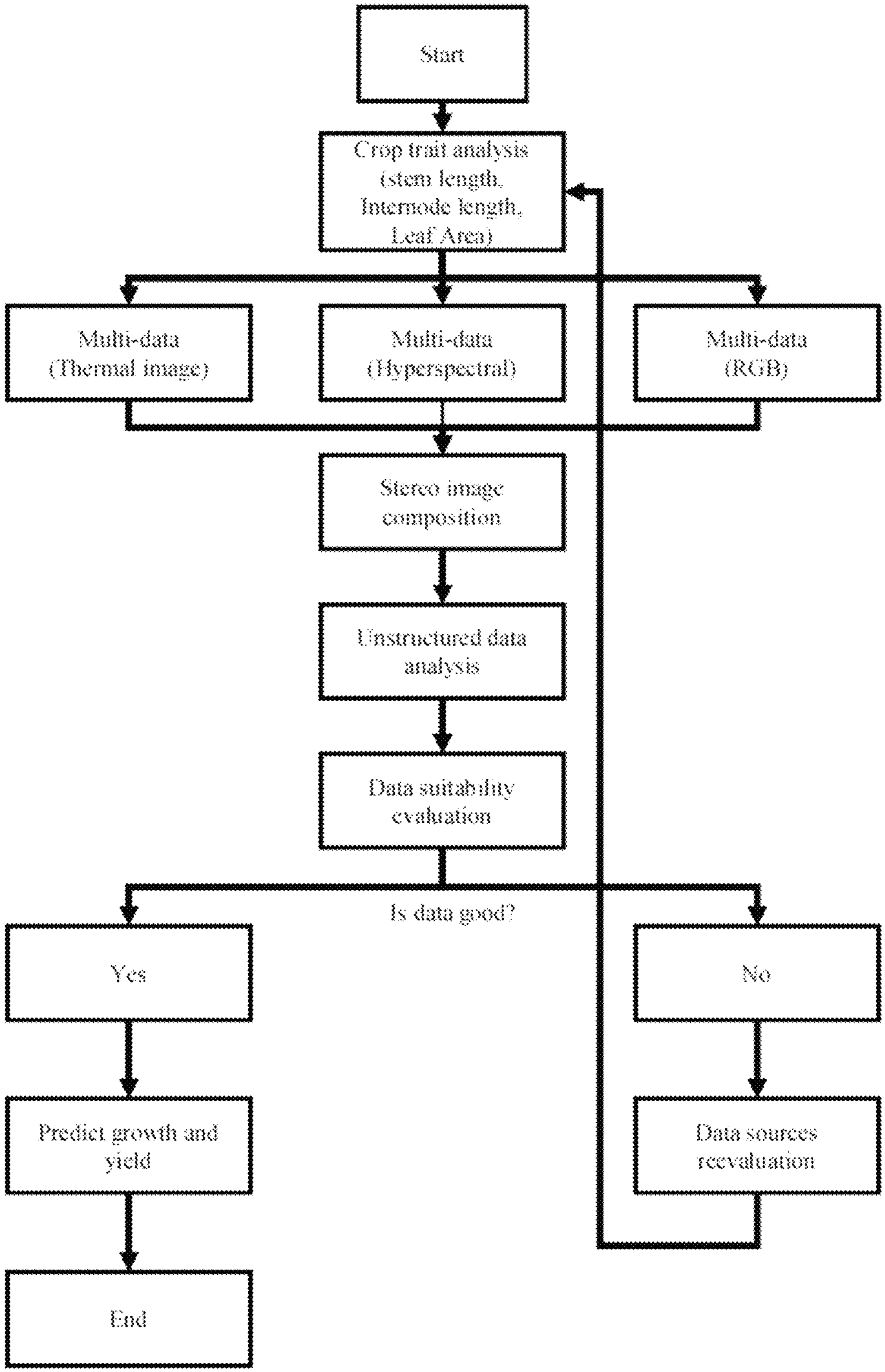
FIG. 6 is a flowchart illustrating the process of collecting and DBing phenotypic data and analyzing the DBed data using the crop growth information analysis apparatus through multiple composite images of the present disclosure.

FIG. 6 is a flowchart illustrating the process of collecting and DBing phenotypic data and analyzing the DBed data using the crop growth information analysis apparatus through multiple composite images of the present disclosure. In order to classify, store, compose, analyze, and use the RGB images, thermal images, and hyperspectral images taken and stored inside the smart farm according to the characteristics of the crops, it is necessary to verify that the RGB images, thermal images, and hyperspectral images are properly taken and may be used in the future. For example, the flowchart shows the process of checking whether the information obtained by taking images of the same crop in the same location is related to each other, whether the crop is not visible in the image due to out-of-focus, light intensity, or the wrong position of the light source, and storing and using it for growth and yield prediction. If it turns out to be a wrong image, retake it, or delete the data so that it doesn’t falsely influence your analysis.

Figure 7:
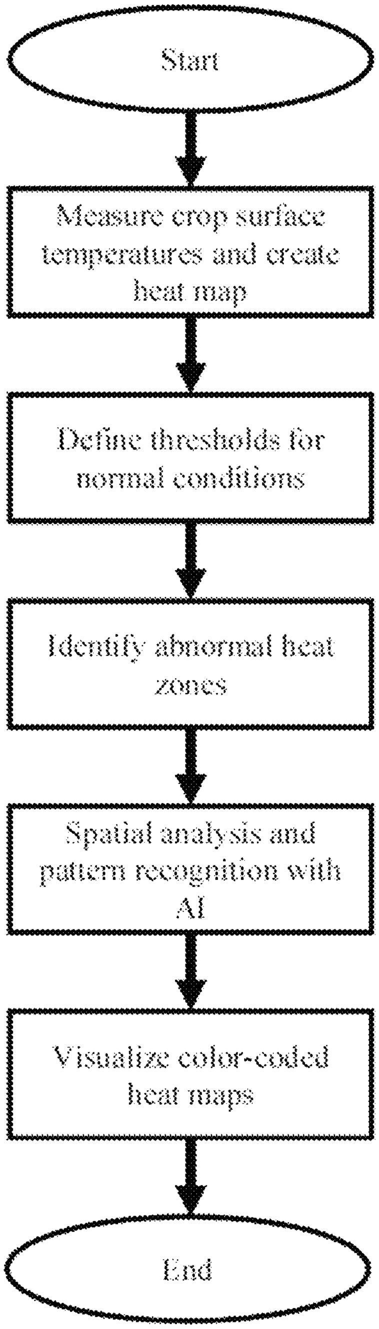
FIG. 7 is a flowchart illustrating a method of analyzing heat stress using the crop growth information analysis disclosure through multiple composite images of the present disclosure.

FIG. 7 is a flowchart illustrating a method of analyzing heat stress using the crop growth information analysis disclosure through multiple composite images of the present disclosure. The location of crops and separation of crops from the background using RGB images and thermal images is performed using RGB images, and at this time, since the image taken from the R (red) CCD among the images taken from each of the R, G, and B CCDs may not be distinguishable from the thermal image, or for accurate analysis, it may be excluded, and a stereo image may be created and used for analysis. RGB and thermal images are combined to measure crop surface temperatures and thermal maps that reflect crop-specific temperature characteristics are generated. Abnormal heat area is identified by setting a threshold temperature that separates crops from heat stress and coloring crops above the threshold temperature in red and below in blue. The identified stereo images are then fed into the AI data analysis part to analyze the growth information and visualize the heat map for the user. If necessary, the abnormal heat area is analyzed to determine whether it is caused by environmental factors such as the installation location of the smart farm or differences in heat resistance according to the genotype of the crop. Experimental groups are created using transplantation methods and further analyzed in separate experiments.

Figure 8:
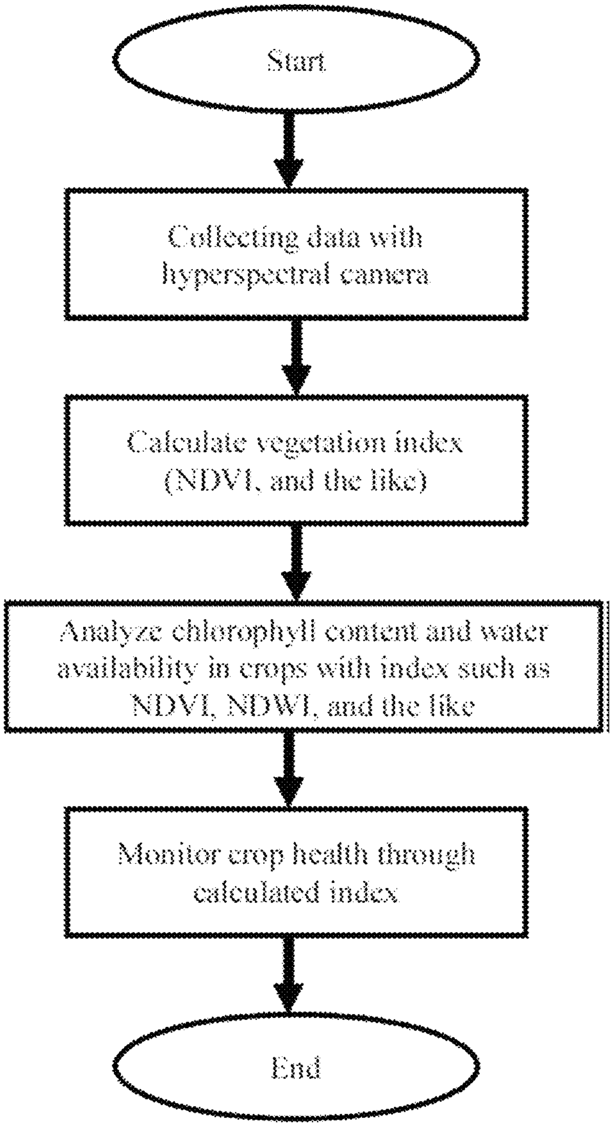
FIG. 8 is a flowchart illustrating a method for analyzing a vegetation index using the crop growth information analysis apparatus through multiple composite images of the present disclosure.

FIG. 8 is a flowchart illustrating a method for analyzing a vegetation index using the crop growth information analysis apparatus through multiple composite images of the present disclosure. The Normalized Difference Vegetation Index (NDVI) is a vegetation index used to quantify vegetation by measuring the difference between near-infrared light, which is strongly reflected by vegetation, and red light, which is strongly absorbed by vegetation. In other words, healthy vegetation (chlorophyll) reflects more near-infrared (NIR) and green light and absorbs more red light than other wavelengths. This is why healthy plants look green to our eyes.

Plant chlorophyll strongly absorbs visible light, and leaf cells strongly reflect near-infrared light. Therefore, observing changes in near-infrared (NIR) compared to red light may provide an accurate indication of chlorophyll status and analyze plant health.

It may be calculated as NDVI=(NIR−RED)/(NIR+RED).

An NDVI value of 0 indicates no green vegetation, while a value of 1 indicates the highest green leaf density.

The RED value uses only the value measured by a CCD that measures RED in the RGB image, and after image analysis of the RGB image, the RED information value corresponding to the location of the crop is only used to accurately calculate the vegetation index of the crop. The NIR value may use an image taken at a light wavelength between 750 nm and 2500 nm, which is the near-infrared region of the hyperspectral image, but preferably an image between 900 and 1100 nm.

Figure 9:
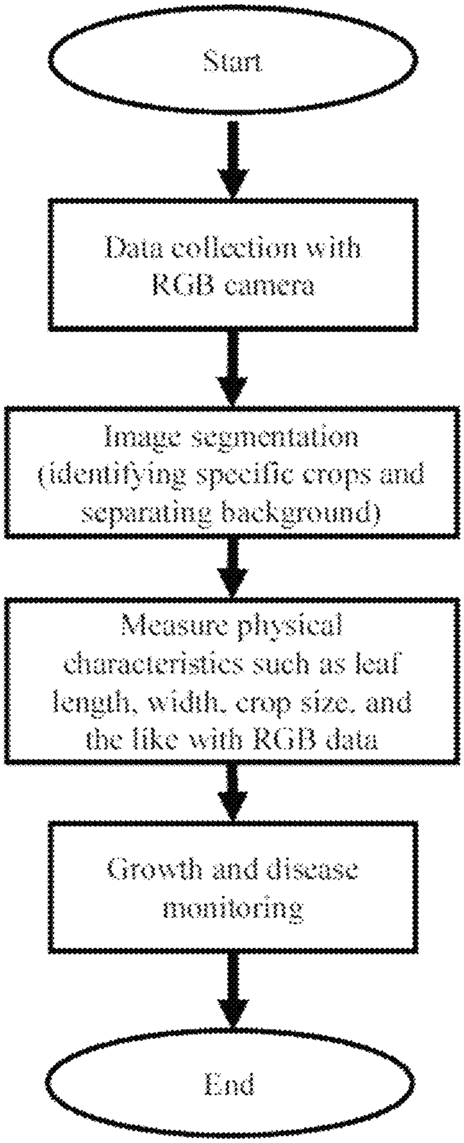
FIG. 9 is a flowchart illustrating a method of analyzing an RGB image using the crop growth information analysis apparatus through multiple composite images of the present disclosure.

FIG. 9 is a flowchart illustrating a method of analyzing an RGB image using the crop growth information analysis apparatus through multiple composite images of the present disclosure.

The RGB camera of the present disclosure has high sensitivity in the dark and uses a camera with separate CCD elements that capture red, green, and blue colors, respectively. This allows images to be taken and stored by color and combined when needed. In other words, the technique includes acquiring images using a three-channel visible light camera, separating the background to separate crops from the acquired images, separating crops by crop individuals from the separated images, and separating phenotypes by finding the parts related to the phenotypes of the separated crop individuals. This extraction information of crop individuals, crop locations, and crop phenotypes is stored and combined with images acquired by other image acquisition techniques to create stereo images that may be used in conjunction with genetic traits associated with said phenotypes. This means that finding phenotypes in RGB images is very important because the same phenotype may have the same or similar crop growth form, tolerance to water stress, yield, and taste and aroma of the harvested crop or fruit. FIG. 9 above shows a flowchart of this process. Of course, we may use video images taken in RGB to monitor crop growth and store them for analysis.

Figure 10:
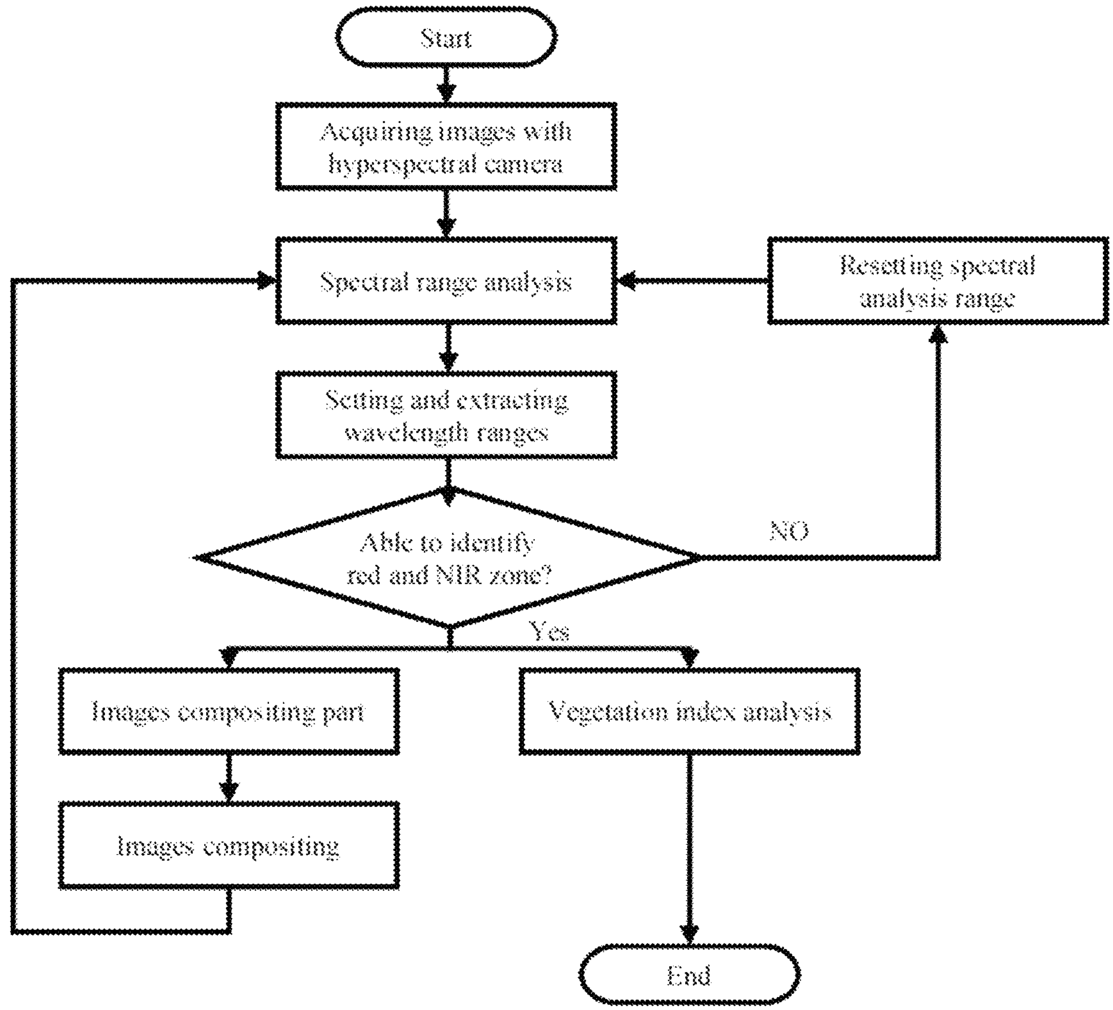
FIG. 10 shows a method of acquiring a hyperspectral image using the crop growth information analysis apparatus through multiple composite images of the present disclosure.

FIG. 10 shows a method of acquiring a hyperspectral image using the crop growth information analysis apparatus through multiple composite images of the present disclosure. Hyperspectral images in the near-infrared region are taken by setting the wavelength band over which the hyperspectral measurements are to be made, and selecting as many wavelengths as possible by increasing or decreasing the wavelength and taking images of the crop in that wavelength band.

Thus, for a point on the crop, for example, information between 750 nm and 2500 nm is measured, and then the information for the point is displayed in a two-dimensional graph, with the selected light wavelength plotted as a horizontal line and the intensity of the reflected light measured at each wavelength plotted as a vertical line. It is possible to reduce the number of wavelengths measured through experimentation and research because it generates too much information, but the more information acquired, the more we may learn about the crop using that information. By selecting and photographing near-infrared light wavelengths between 900 and 1100 nm, chlorophyll, that is, vegetation index may be measured; the near-infrared wavelength region between 1200 and 1300 nm may be selected to identify insect and bug larvae and eggs; and transpiration of crop leaves may be detected by measuring hyperspectral images using the 3000 nm near-infrared wavelength. In other words, if the leaves of a crop are warming up on a thermal camera in the presence of sunlight, hyperspectral images in the 3000 nm band may be used to determine if transpiration is occurring, which is the release of water from the leaves of the crop, and may be used to create a water stress index.

Figure 11:
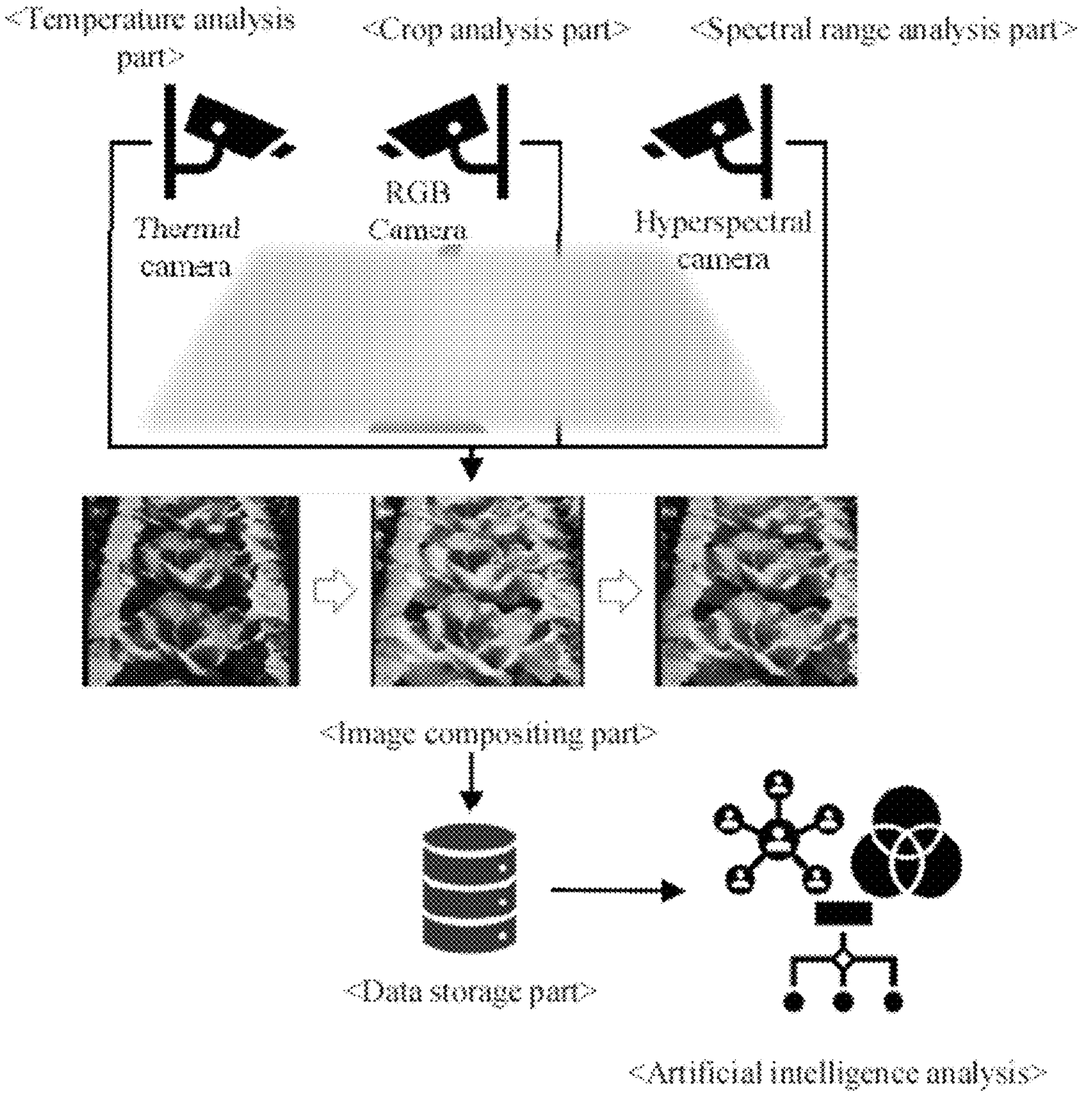
FIG. 11 is a conceptual diagram of the overall system configuration of the crop growth information analysis apparatus using the multiple composite images of the present disclosure.

FIG. 11 is a conceptual diagram of the overall system configuration of the crop growth information analysis apparatus using the multiple composite images of the present disclosure. It is one example embodiment of the present disclosure to take multiple images of a smart farm or open field crop using an RGB camera, a thermal camera, and a hyperspectral camera; check with an artificial intelligence image verification algorithm whether the images contain information about the crop; then, compose the images taken by two or more apparatuses to generate a stereo image; database and store the generated stereo image; and input the stereo image to an artificial intelligence model in real time or non-real time to make a yield prediction and a growth prediction based on the growth status, growth rate, pest, and phenotype of the crop.

EXPLANATIONS OF SYMBOLS

100: Growth information analysis apparatus
110: Temperature analysis part
111: Thermal camera
120: Spectral range analysis part
121: Hyperspectral camera
130: Crop recognition part
131: RGB camera
140: Image composition part
141: Heat stress analysis
142: Vegetation index analysis
143: RGB analysis
150: Data storage part
160: Artificial intelligence analysis

What is claimed is:

1. An apparatus for analyzing crop growth information through multiple composite images, the apparatus comprising:

a thermal imaging camera and a temperature analysis part for analyzing the temperature from images acquired by the thermal imaging camera;

a hyperspectral camera and a spectrum analysis part for analyzing a range of spectrum from images acquired by the hyperspectral camera;

a RGB camera and a crop recognition part that recognizes crops distinctly between the background and foreground of the images acquired by the RGB camera;

an image merging part for generating a single merged image from an image acquired by the thermal imaging camera, an image acquired by the hyperspectral camera and an image acquired by the RGB camera; an image compositing part that creates multiple composite images using the image merged from the image merging part;

a data storage part that stores the image composited by the image compositing part and the merged image merged by the image merging part; and an artificial intelligence analysis part that classifies the merged image stored in the data storage part by phenotype of the crop using images stored in the data storage part and builds a database (DB).

2. The apparatus and the method of claim 1, wherein the image compositing part comprises:

a heat stress analysis part that analyses heat stress using the thermal image and crop data recognized by the crop recognition part; and a RGB analysis part performs RGB analysis using the RGB image.

3. The apparatus and the method of claim 2, wherein the RGB analysis part extracts trait information of the crop to analyze characteristics of the crop according to the phenotype of the crop.

4. The apparatus and the method of claim 3, wherein the trait information of the crops comprises stem length, internode length, leaf width and leaf length.

5. The apparatus and the method of claim 4, wherein information combined with the crop trait information comprises fruit size, number, heat stress and vegetation index.

6. The apparatus and the method of claim 5, wherein the data storage part stores the merged image, along with a crop type, a water stress index, growth index, a leaf length, a leaf width, a leaf height, a crop surface temperature, a medium temperature, images date, an external temperature and humidity, a smart farm internal temperature and humidity, a crop number, and a crop location.

* * * * *